United States Patent
Hartung

(10) Patent No.: US 8,411,111 B2
(45) Date of Patent: Apr. 2, 2013

(54) MODEL GENERATOR FOR CARDIOLOGICAL DISEASES

(75) Inventor: Ulrich Hartung, Langensendelbach (DE)

(73) Assignee: Siemens Aktiengesellschaft, Munich (DE)

( * ) Notice: Subject to any disclaimer, the term of this patent is extended or adjusted under 35 U.S.C. 154(b) by 558 days.

(21) Appl. No.: 12/654,340

(22) Filed: Dec. 17, 2009

(65) Prior Publication Data

US 2010/0156904 A1  Jun. 24, 2010

(30) Foreign Application Priority Data

Dec. 23, 2008  (DE) .......................... 10 2008 062 857
Jan. 26, 2009  (DE) .......................... 10 2009 006 147

(51) Int. Cl.
*G09G 5/00* (2006.01)

(52) U.S. Cl. ........ 345/629; 345/419; 345/420; 345/581; 345/619; 345/646; 382/128; 600/407; 600/436; 600/437

(58) Field of Classification Search .................. 600/437, 600/407, 436; 382/128
See application file for complete search history.

(56) References Cited

U.S. PATENT DOCUMENTS

| | | | |
|---|---|---|---|
| 6,563,941 B1 | 5/2003 | Schmuel et al. | |
| 7,894,647 B2 * | 2/2011 | Zhou et al. | 382/128 |
| 7,991,594 B2 * | 8/2011 | Unal et al. | 703/2 |
| 8,036,441 B2 * | 10/2011 | Frank et al. | 382/131 |
| 2002/0172403 A1 * | 11/2002 | Doi et al. | 382/128 |
| 2004/0215071 A1 * | 10/2004 | Frank et al. | 600/407 |
| 2005/0080328 A1 * | 4/2005 | Vass et al. | 600/407 |
| 2007/0156047 A1 * | 7/2007 | Nagler et al. | 600/436 |
| 2007/0189591 A1 * | 8/2007 | Lu et al. | 382/128 |
| 2007/0244393 A1 * | 10/2007 | Oshiki et al. | 600/463 |
| 2008/0008369 A1 * | 1/2008 | Koptenko et al. | 382/128 |
| 2008/0094389 A1 * | 4/2008 | Rouet et al. | 345/419 |
| 2009/0092301 A1 * | 4/2009 | Jerebko et al. | 382/128 |
| 2009/0274350 A1 * | 11/2009 | Pavlovskaia et al. | 382/128 |
| 2009/0297012 A1 * | 12/2009 | Brett et al. | 382/132 |
| 2010/0246910 A1 * | 9/2010 | Wiemker et al. | 382/128 |
| 2010/0259546 A1 * | 10/2010 | Yomdin et al. | 345/473 |
| 2011/0190629 A1 * | 8/2011 | Guenther et al. | 600/437 |

OTHER PUBLICATIONS

West, R. M., & Williams, R. A. (Apr. 1999). Opportunities for data fusion in multi-modality tomography. In Proc. 1st World Congress on Industrial Process Tomography (pp. 195-200).*

Archivierungsprotokoll des Internet-Archivs http://web.archive.org/ zu den zitierten Dateien 3d-doctor.com/manual1.pdf, 3d-doctor.com/ manual2.pdf, 3d-doctor.com/manual3.pdf(abgerufen am Jun. 21, 2010); Others.

3d-doctor User's Manual, Able Software Corp., Jan. 10, 2008. URL: http://www.3d-doctor.com/manual.pdf, (abgerufen am Jun. 17, 2010); Others.

German Office Action dated Jun. 30, 2010.

(Continued)

*Primary Examiner* — Xiao M. Wu
*Assistant Examiner* — Phi Hoang
(74) *Attorney, Agent, or Firm* — Harness, Dickey & Pierce, P.L.C.

(57) ABSTRACT

At least one embodiment of the present invention relates to a method, a device and/or a computer program product for creating a (three- or four-dimensional) model from a number of different image datasets from a number of modalities. To this end, in at least one embodiment, the image datasets are fitted into a representation provided, the different image datasets being automatically enriched with contour lines and integrated into the representation. The model is created from this.

20 Claims, 5 Drawing Sheets

OTHER PUBLICATIONS

"3d-doctor" image processing software. Manual. Able Software Corp., 2004. URL: http://web.archive.org/weg/20041022061735/3d-doctor.com/manual2.pdf, archiviert in http://www.archive.org am Oct. 22, 2004 (called up Dec. 18, 2009), section 1, 3.4, 3.7 and 3.12., URL: http://web.archive.org/weg/20041022061735/3d-doctor.com/manual3.pdf, archiviert in http://www.archive.org am Oct. 22, 2004 (called up Dec. 18, 2009), section 5.1 bis 5.3.; Others; 2004.

* cited by examiner

MODEL GENERATOR FOR CARDIOLOGICAL DISEASES

PRIORITY STATEMENT

The present application hereby claims priority under 35 U.S.C. §119 on German patent application numbers DE 10 2008 062 857.3 filed Dec. 23, 2008 and DE 10 2009 006 147.9 filed Jan. 26, 2009, the entire contents of each of which are hereby incorporated herein by reference.

FIELD

At least one embodiment of the present invention generally lies in the areas of information technology and medical technology and at least one embodiment relates in particular to a method, a device and a computer program product for creating a (three-dimensional) model from a number of different image datasets as part of a medical diagnosis.

BACKGROUND

As part of diagnostics and therapy planning for different diseases and especially of complex cardiological and pediatric cardiological illnesses the doctor is confronted with a plurality of image datasets from a number of different methods. Typical examples that could be mentioned here are heart ultrasound examinations, heart catheter examinations, nuclear magnetic resonance tomographies and computed tomographies and further examinations that provide information about a functional interrelationship between the organs to be examined. The plurality of the image datasets that originate as a rule from different modalities, must all be taken into account by the doctor undertaking the study to enable him to produce an overall statement.

It is evident that this work requires a high degree of care and that there should be a way of excluding errors, since in some cases this can have life-threatening results for the patient. Practice shows however that in the current prior art method errors can unfortunately not be excluded, since the plurality of individual findings obtained imposes an enormous demand on the doctor. In such cases he must identify the medically-relevant data present in the individual results and transfer it to the image information of the other modalities.

Previously the merging of the different individual results was undertaken manually by the doctor. Thus there was previously provision for image datasets to be acquired at each modality (e.g. MRT, CT, ultrasound etc.) and to be analyzed by the radiologist and/or by the pediatric cardiologist. After this analysis is concluded a medical report is generally created which can either be structured as pure text or with embedded images. The pediatric cardiologist then collects this information and analyzes this based on his or her medical expertise, generates a diagnosis and/or decides on the further course of the diagnosis or of the further treatment. The results of the imaging and the generation of the report can in this case be undertaken by medical specialized diagnosis software. In such cases the modality-specific information can be present in a three-dimensional image dataset or even in a four-dimensional image dataset (which includes a development over time and thereby a functional development).

In practice the difficulty now confronting the examining doctor is that of combining or merging the image datasets provided by the different modalities. The combining or merging of the modality-specific image datasets has previously had to be undertaken manually by the doctor. The doctor is only supported by information technology for congenital anomalies within the framework of specialized diagnosis software, for example in products such as PedHeart® and PedCath®. This software is especially suitable for investigating specific pediatric-cardiological diseases, such as a Fallot's tetralogy a transposition of the large arteries and/or uncorrected shunt vities. There is therefore a demand for a further information technology and automated support in merging image datasets from different modalities into three- and/or four-dimensional modeling of anatomical structures as part of an examination and/or diagnosis.

SUMMARY

In at least one embodiment, the present invention has therefore set itself the task of demonstrating a way with which a model can be created from medical image datasets, with the image datasets being patient-specific and modality-specific and originating from different modalities. In these cases the different image datasets will be merged into a three- or four-dimensional model which will then be presented. In such cases the modeling of three- or four-dimensional volume datasets is to be carried out across different modalities.

This may be achieved by a computer-implemented method, a device and/or a computer program product.

An embodiment will be described below in relation to the method. Features, advantages or alternate embodiments mentioned here are also to be transferred to the other embodiments and vice versa. In other words the physical claims (which are directed to a device for example) can be developed with the features which are described or claimed in conjunction with the method and vice-versa. The corresponding functional features of the method will be embodied in such cases by corresponding physical modules, especially by hardware modules, of the device.

At least one embodiment is directed to a computer-implemented method for creating a (three- or four-dimensional) model from a number of medical image datasets, comprising:

Provision of a number of image datasets with the image datasets being acquired or having been acquired from the same or from different modalities;

Automatic creation of contour lines in the image datasets provided;

Provision of a (three- or four-dimensional) representation for the image datasets—preferably from a model archive;

Semi-automatic fitting of the created contour lines into the representation provided and merging of the image datasets provided for calculating the model for the image datasets;

Presenting the (patient specific) model for the image datasets.

The terms which will be used within the context of this application are explained in greater detail below.

The "model" involves a three-dimensional or four-dimensional representation of the organ to be examined such as the heart for example. With the four-dimensional model, information about the time or functional information is additionally included, such as pump information of the heart for example, blood pressure conditions and/or blood flow directions (e.g. in relation to the heart valves) or information about the blood speed. If the organ to be examined does not involve the heart, other functional variables can be recorded in relation to the respective organ, such as the sampling of bile etc for example. With a four-dimensional model relating to the heart, EKG information or further parameters in relation to the time can also be integrated for example. The model is patient-specific and covers a number of modalities. The model is additionally a graphical representation of different image datasets (which have been acquired from different modalities) and which will be integrated into a model. The model serves to make the examination easier for the doctor and will be presented at a user interface as a graphical 3D representation.

The medical image datasets involve datasets from the different modalities such as datasets from a magnetic resonance examination for example, from a computed tomography, an ultrasound examination, laboratory investigations, from a heart catheter examination or the like. In addition a number of examination results can also be merged into one image dataset. The image datasets can be acquired online in real time so to speak or they can already be recorded in a previous examination and will be retrieved from a memory.

The contour lines involve graphical framing and thereby restructuring aids in the image dataset. The organ to be presented is contoured by the contour lines and if necessary segments of the organ can likewise be worked out with contour lines. The contour lines serve to better identify the organ presented. The contour lines delimit the organ in relation to the adjoining and surrounding tissue. Conventional computer-aided products can be employed for creating the contour lines, in particular standard methods within the framework of pattern matching and pattern recognition will be used here.

At least one embodiment of the invention also uses a representation for the image datasets. The representation involves an abstracted three-dimensional or four-dimensional display of the organ to be examined. The representation is abstracted from the respective patient and does not include any patient-specific information. The representation will as a rule be created from a number of patient-specific image datasets and serves so to speak as a basic framework or as a pattern for (three- or four-dimensional) representation of the respective organ. Thus for example a three-dimensional representation of an adult healthy heart is provided, a three-dimensional representation of a child's heart at a specific age, and a further three-dimensional representation of a heart with a specific disease. The representations can be stored in an archive (representation archive). In addition the representations can be modified at any time and/or be supplemented by further representations.

By contrast with a representation, a model involves a patient-specific model which is based on the respective examinations of the patient. Integrated in the model are all previous examinations relating to the patient and to the organ to be examined. To this end all available image datasets are combined. The calculated model is preferably displayed at a graphical user interface.

In accordance with an example embodiment of the present invention the image datasets are two-, three-, and/or four-dimensional. However two embodiments are primarily provided:

A first embodiment is based on the number of two-dimensional image datasets from different modalities being present which will be integrated into a three-dimensional model.

A further option is to be seen in the three-dimensional volume datasets already being present, which will likewise be integrated into a three- or four-dimensional model. This involves a refinement of an existing three-dimensional model or an integration of a number of three-dimensional datasets into a four-dimensional model.

In accordance with an advantageous development of an embodiment of the present invention there is provision, in the (three-dimensional) representation and/or in the calculated model for further image datasets to be able to be fitted in—even retrospectively. This enables follow-up examinations to be integrated into a simple manner into the previously created patient-specific model and the doctor can thus easily obtain an overview of all examinations previously undertaken.

In accordance with a further embodiment of the present invention, there is provision for the creation of the contour lines to be undertaken automatically. As an alternative or in addition to this it is however possible at any time for the user to adapt the automatically-generated contour line manually. This enables errors and consequential errors to be avoided. The user is also given a suggestion for creating the contour lines that he can accept, modify or reject.

In accordance with a development of an embodiment of the invention there is provision for the provision of the image datasets to include an automatic adaptation of presentation parameters. The presentation parameters involve all parameters that are relevant in relation to the display or in relation to the presentation of the model. This especially includes size relationships, the resolution, the size of the respective window, the number of integrated image datasets, the dimension of the model (three- or four-dimensional).

As already mentioned above there is provision for the model to preferably be three-dimensional. An advantageous further development is embodied slightly more complex and makes provision for a four-dimensional model, so that further time-dependent information is able to be derived here.

Furthermore the model includes information covering a number of image datasets. This means information that can only be derived from a combination of different image datasets and is not available solely in one individual image dataset. This typically involves pump information of the heart, blood pressure conditions, blood flow direction information, blood speed information and likewise further parameters such as oxygen saturation of the blood for example, information in respect of tissue healing etc. The advantage of this is that the doctor is supplied with yet more relevant information about the organ to the examined.

In accordance with the further advantageous embodiment, there is provision for the model to include absolute size information (for example specified in centimeters). Open above this relative size information can also be included (such as the relation to adjoining organs or of the relation to size conditions on a healthy organ compared to an unhealthy organ etc. for example).

An advantageous development of an embodiment of the invention is to be seen as the method being carried out the semi-automatically. This means that the user can manually enter further (two-dimensional) image datasets into the three-dimensional representation. In addition only a suggestion for the calculated model is created that can be further refined or modified by the user. This is normally done via user entries that the user makes at a graphical user interface (typically with the mouse). Here for example the two-dimensional image datasets can be pulled to the correct position within the three-dimensional representation. The calculated model can thus still be modified or adapted by the user.

In accordance with an advantageous embodiment the model is editable (for example to enable the user adaptation to be undertaken) and/or the model is navigable. "Navigable" in this context means that the user can navigate within the calculated and presented model. In particular he can mark specific areas here with the mouse at which the assigned image datasets will then be displayed to him.

In accordance with an advantageous development the calculation of the model is based on an interpolation. Previously fitted-in contour lines are interpolated to further slices in the three-dimensional representation. This means that the model can be successively refined.

In accordance with a further embodiment of the present invention the calculated model will be stored unchanged or changed as a basis for a further representation in an archive. Likewise models stored in the archive can be used for other methods.

A further object of at least one embodiment of the invention consists of a computer-implemented device for creating a model from a number of medical image datasets, comprising:

At least one input interface to a number of different modalities, with the modality being intended to provide at least one image dataset, and with the image datasets from the same or from different modalities being acquired or having been acquired via the input interface;

At least one contour module designed for automatic creation of contour lines in the image datasets provided, which have been received via the input interface;

An archive intended for provision of at least one representation of image datasets (received via the input interface) Image datasets;

An integrator designed for semi-automatic fitting of the created contour lines into the representation provided and for merging the image datasets provided for the purposes of calculating the model for the image datasets;

A graphical user interface which is designed for displaying the calculated model for the image datasets.

The input interface is used for access to image datasets of modalities. All image datasets of different modalities are fed to the inventive device via the input interface. To this end the input interface can either access a central data memory, in which all image datasets of different modalities are collected or the input interface is designed so that it accesses the memory of the respective modalities directly.

The contour module is embodied to integrate at least one contour line into the image dataset in the recorded image datasets. The contour line serves to delimit the respective organ from its environment and can for example involve the contour of the stomach, the contour of the heart, the contour of the liver etc. The contour line will be integrated into the image dataset. The contour line can also identify segments of the respective organ, such as the heart chambers, the heart arteries etc. for example.

The archive serves to provide at least one patient-independent representation. In this representation all patient-dependent information is evened-out, relativized and/or generalized and an abstract model will be created for a respective organ or for a specific image dataset. Preferably this representation is three-dimensional. In accordance with an advantageous further development of the invention this representation is four-dimensional and additionally includes time-dependent information, for example blood flow specifications or movement specifications.

The integrator is used for fitting the image datasets provided into the representation provided. In other words the different two-dimensional image datasets (ultrasound, heart catheter etc) are preferably integrated by the integrator into the three-dimensional representation. This will preferably be done via the contour lines created, by the created contour lines being inserted into the representation provided. Alternately the user can also use other landmarks or identifiers for fitting. Preferably the fitting of individual slices is undertaken manually. The slices between the manually-fitted slices can however be fitted automatically by interpolation. Furthermore the integrator is also used for combining or merging the different image datasets into a (patient-specific) model. The graphical user interface serves to display the generated patient-specific (three-dimensional or four-dimensional) model. At least one embodiment of the inventive device can be embodied as a hardware module. The units of the device (e.g. the contour module, the integrator) can alternately also be integrated as a software module into the device.

In a more complex embodiment of the invention, the inventive device is integrated into an examination system which supports the user and offers a combined visually-improved presentation of a number of (different) findings.

In a more simple embodiment of the computer-implemented device this is only embodied with one input interface for receiving the image datasets, with a contour module and with a further interface for transferring the representation and with an integrator. The integrator then supplies a result for the device which consists of the generated model. The model can be displayed via a graphical user interface connected to the device.

The inventive embodiments of the method described above can also be embodied as a computer program product, with the computer being caused to execute the inventive method described above when the program is executed on a computer or a processor of the computer.

An alternate solution provides for a storage medium that is intended to store the computer-implemented method described above and is able to be read by a computer.

In addition it is possible for individual components of the method described here to be able to be executed in a commercially-available unit and for the remaining components to be executed in another commercially-available unit—as a distributed system so to speak.

BRIEF DESCRIPTION OF THE DRAWINGS

In the more detailed description of the figures given below example embodiments with their features and further advantages, which are not to be understood as being restrictive in any way, are discussed with reference to the drawing. The figures show.

DETAILED DESCRIPTION OF THE EXAMPLE EMBODIMENTS

Figure 1:
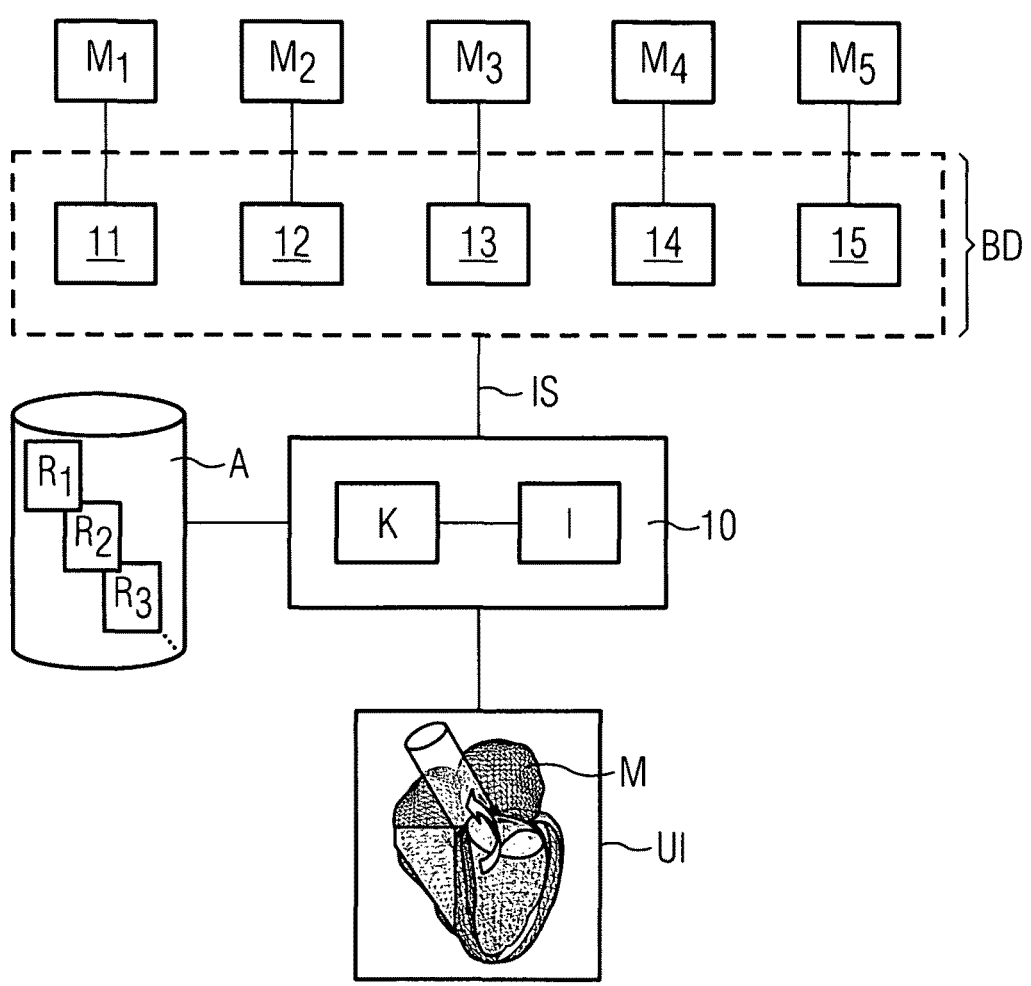
FIG. 1: an overview-type diagram of an inventive device in accordance with an example embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The underlying concept of an example embodiment of the present invention will be explained in greater detail below in conjunction with FIG. 1.

Shown in FIG. 1 is an example embodiment of an inventive device 10 for creating a model M. The model M is preferably three-dimensional. In an advantageous development the model M can also be four-dimensional and can include additional dynamic information, especially time information. This can be correlated in relation to time-dependent image datasets BD. Time-dependent image datasets BD can be EKG image datasets BD for example.

The image datasets BD originate from different modalities. As an alternative or cumulatively the image datasets BD can also be assigned to different examinations of a patient at one and the same modality M. In the example shown in FIG. 1 a first modality $M_1$ is an ultrasound device that creates two-dimensional image datasets, a second modality $M_2$ is a heart catheter and a third modality $M_3$ a nuclear magnetic resonance device which all create two-dimensional image datasets BD. In addition a fourth modality $M_4$ is shown which generates three-dimensional image datasets BD, for example CT image datasets and/or MR image datasets BD. Also shown in FIG. 1 is a fifth modality $M_5$ which creates time-dependent image datasets BD and can typically be an EKG device.

An important aspect of an embodiment of the present invention is to be seen in the fact that the different image datasets BD—i.e. the image datasets from different modalities and/or different image datasets from one and the same modality M—will be integrated into a model M.

The different image datasets BD are read in via an input interface IS and forwarded to the device 10.

The device 10 serves to create the model M from the different image datasets BD. To this end the device includes a contour module K and an integrator I. The contour module K is used for automatic generation of contour lines KL in the image datasets provided. In each image dataset BD provided a contour line KL will thus be created automatically or a suggestion will be generated automatically for a contour line KL that the user can then further modify or adapt. The contour line KL is for example to be seen in the image dataset BD depicted at the bottom left of FIGS. 3 and 4 respectively. The contour line KL is used in marking the contour of the respective organs or of their respective region of the body that is to be examined. The contour line KL will be integrated into the image dataset BD.

In addition the device 10 includes the integrator I that is designed for semi-automatic fitting of the image dataset BD to the contour line KL. The image datasets BD with the automatically-created contour lines KL will be integrated in this case into a representation R.

The representation R is a patient-independent general representation of the respective organs or of the respective segment of the body. For example there are representations R for the heart, for the liver, for the stomach and different representations can also be created for different patient types (for example for children, for adults, for women and for men or representations for specific diseases). The representation R is preferably three-dimensional. Alternately it can also be four-dimensional and include time information. The representations are preferably stored in an archive A and can be expanded at any time by additional representations R.

The Integrator I comprises a processing unit which, from the image datasets BD provided with their respective contour lines KL and a first semi-automatic fitting into the representation R provided, creates a model M.

In accordance with an advantageous development of at least one embodiment of the invention there is provision for the contour lines KL to be suggested automatically. To this end the suggested contour line KL is shown on the image dataset BD. The image dataset with the contour line KL can however also be manually adapted by the user so that it is made possible for the user to obtain a modeling of the contours that is realistic and adapted to the current situation. The user can thus still vary, distort or move the automatically-suggested contour lines KL manually. This manual post-processing or adaptation is possible independently of the underlying raw image data BD. The adaptations (manual or automatic) can be stored as an additional dataset so that all changes are still able to be verified. In addition to the manual adaptation of the contour lines KL on the part of the doctor or the user, an automatic adaptation of the contour lines KL is also provided which is based for example on the known mechanisms of image processing such as object recognition, rendering or on other methods from medical information technology.

As shown in FIG. 1, a user interface (UI) is also provided at which the generated model M will be displayed.

A further significant aspect of an embodiment of the present invention is to be seen in the fact that the generated model M is editable. In addition the user can also navigate in the created model M, by selecting individual slices in the three-dimensional model M for example, in order to display a corresponding two-dimensional slice. In addition all graphical functions can be executed on the model M. Typically the model M can be rotated, cut, distorted and/or transformed in any manner. Likewise different directions of view can be assumed (four-chamber view, two-chamber view, longitudinal axis etc. in the display of a model M for the heart for example).

Figure 2:
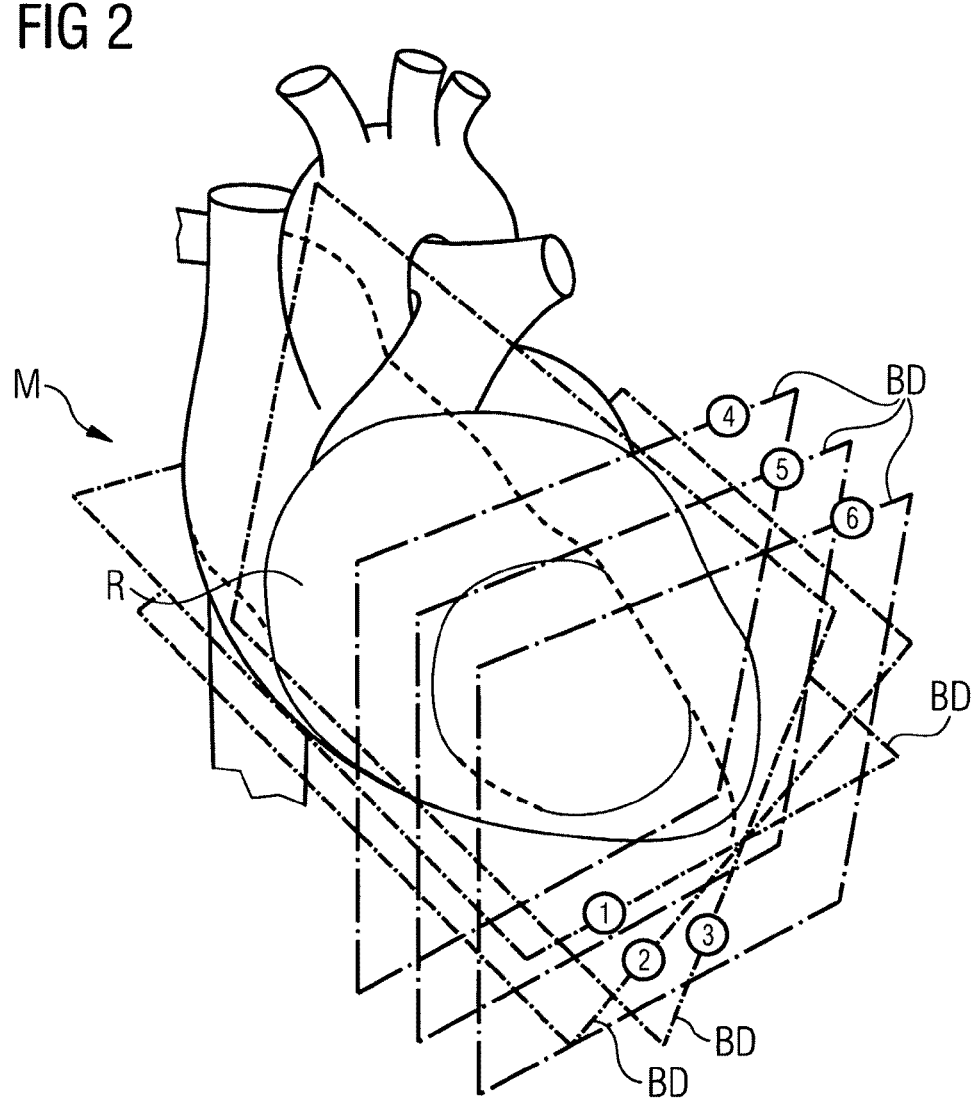
FIG. 2: schematic diagram of a generated three-dimensional model in accordance with an example embodiment of the invention.

FIG. 2 shows a schematic diagram of a three-dimensional model M, into which different two-dimensional slices have been fitted. In FIG. 2 the respective slices are identified by the numbers 1 through 6. The numbers relate to the different slices which will be explained in greater detail below.

In FIG. 1
the slice labeled "1" identifies a four-chamber view,
the slice labeled "2" identifies a two-chamber view,
the slice labeled "3" is intended to show a so-called "longitudinal axis" of the heart,
the slice labeled "4" is a so-called "basic slice",
the slice labeled "5" is a slice through the middle of the heart, and
the slice labeled "6" is the apex slice of the heart.

In the example embodiment a semi-automatic method is provided for inserting the respective slices into the representation R. In this case the doctor must define the positions and which the respective two-dimensional image must be inserted into the three-dimensional representation. As already mentioned above, the model can also involve a four-dimensional model so that time-dependent information can be additionally included in the model M.

Figure 3:
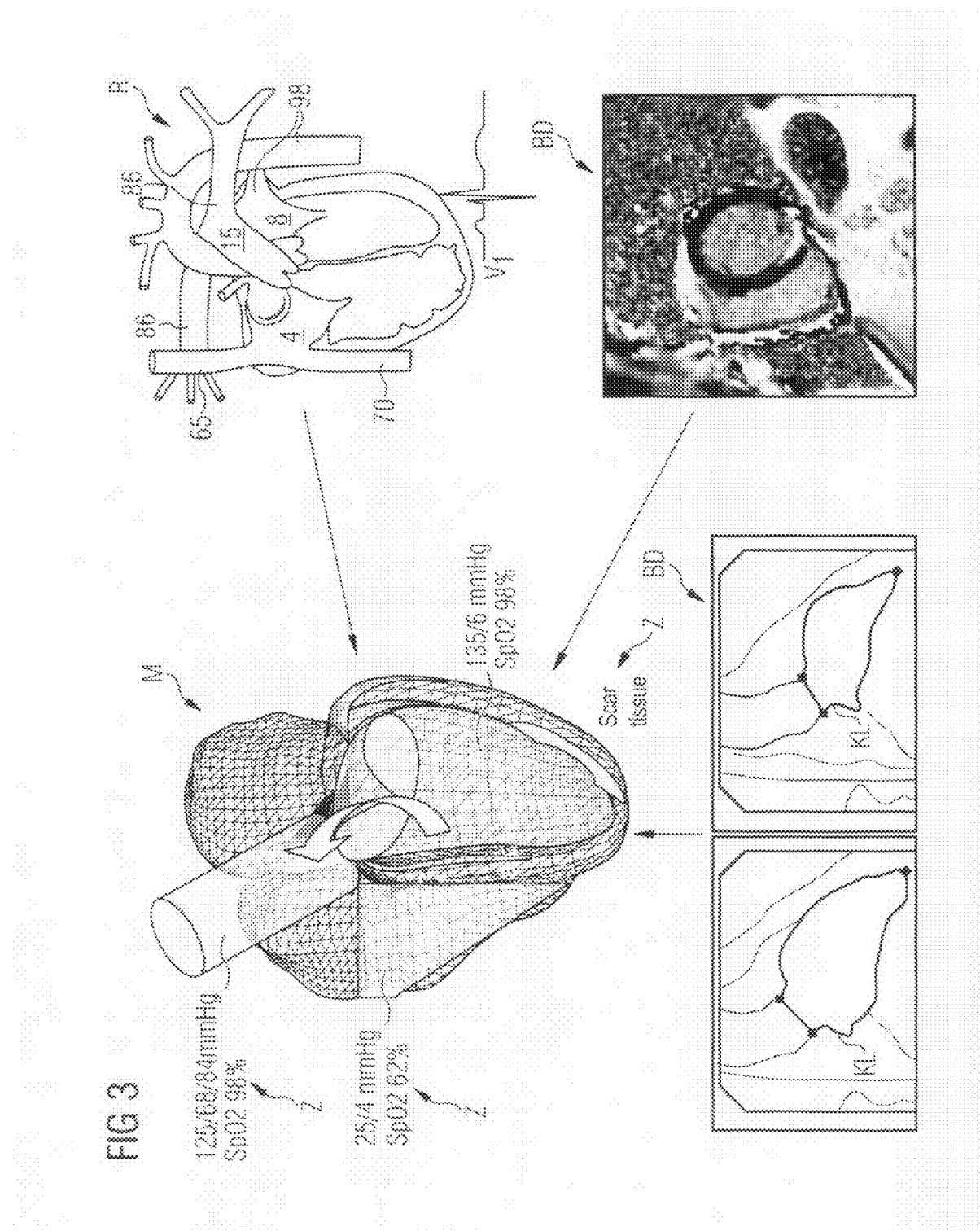
FIG. 3: typical drawing of different image datasets and a representation that will be used to generate a model.

Shown in the lower part of FIG. 3 are different image datasets BD which will be integrated into the model M shown at the top left in FIG. 3. The representation R which is shown at the top right in FIG. 3 will also be used in addition to the image datasets BD.

Figure 4:
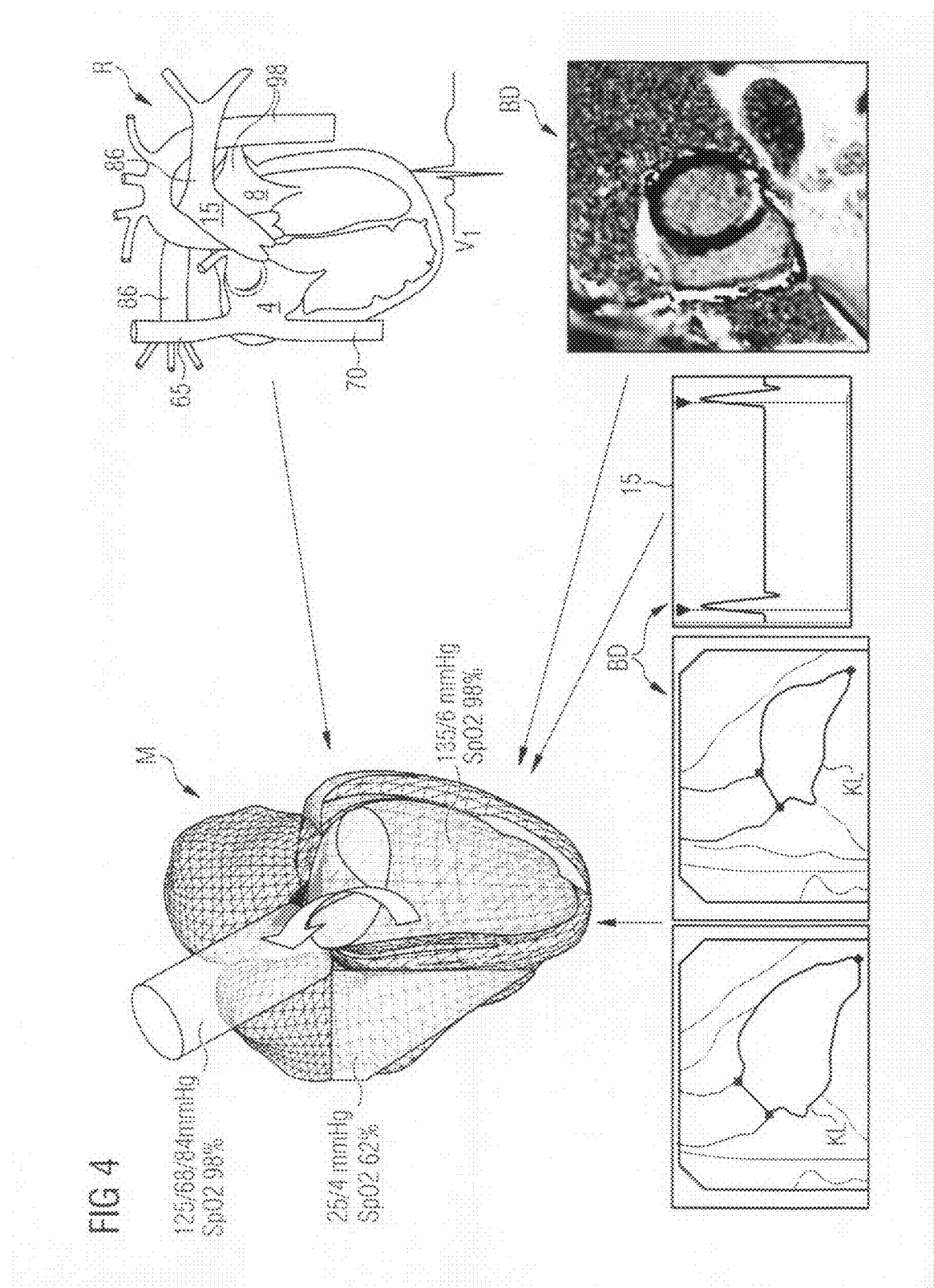
FIG. 4 is an expansion of the drawing depicted in FIG. 3, with the model from FIG. 3 being shown with other dynamic datasets correlated to the EKG.

As can be seen in FIGS. 3 and 4, the representation R involves a schematic diagram of specific segments of the body or organs. In a development of the invention the representation R can be embodied with additional information. This is intended to be represented in the representation R depicted in FIGS. 3 and 4 by the numbers contained in the circles. The numbers can relate to different parts of organs and serve to simplify identification of the parts of the organs for the user. To this end a concordance list can be shown on the screen which names the respective part of the organ for each number.

All this information will be used for computing the three- or four-dimensional model M that is shown at the top left of FIG. 3.

The model M comprises a three-dimensional representation of the respective organ and can also comprise further information Z encompassing a number of image datasets. The information Z comprising a number of image datasets can for example be information about the structure of the tissue (e.g. diseased tissue or healthy tissue), about oxygen saturation (e.g. as a percentage figure) or further additional information. The information Z encompassing a number of image datasets can also relate to information about blood and the pump information of the heart, blood pressure conditions and/or the direction of blood flow or the blood speed. The information Z encompassing a number of image datasets can be determined from an individual image dataset BD.

In addition it is possible for the information Z encompassing a number of image datasets to be determined from the combination of the different image datasets (therefore the expression "encompassing a number of image datasets"). Likewise it is possible for the user to also insert manual information Z via a corresponding user interface (e.g. particular labels such as, "N.B: symptom of occlusion?"). Likewise the model M can include absolute and/or relative specifications. These specifications can for example involve absolute size specifications of the organ displayed. In addition relative size specifications can be provided in relation to adjacent organs.

In the example of the model M shown in FIG. 4 the model M is also expanded by a further image dataset 15 that relates to EKG data. The image datasets BD will be correlated with the EKG image datasets and integrated into the model M.

In FIGS. 3 and 4 the information Z encompassing a number of image datasets is embodied for example as textual specifications. Over and above this, colors or other means of highlighting or specific encodings of the respective segment can be provided. For example a higher oxygen saturation can be represented by a red coloring whereas a lower oxygen saturation can be represented by a blue coloring. The textual specifications of the additional information Z are for example in FIGS. 3 and 4: "125/68/84 mmHg—$SpO_2$ 62%". Depending on the respective default setting, the model M can however be supplemented with any other or further type of given additional information Z.

Figure 5:
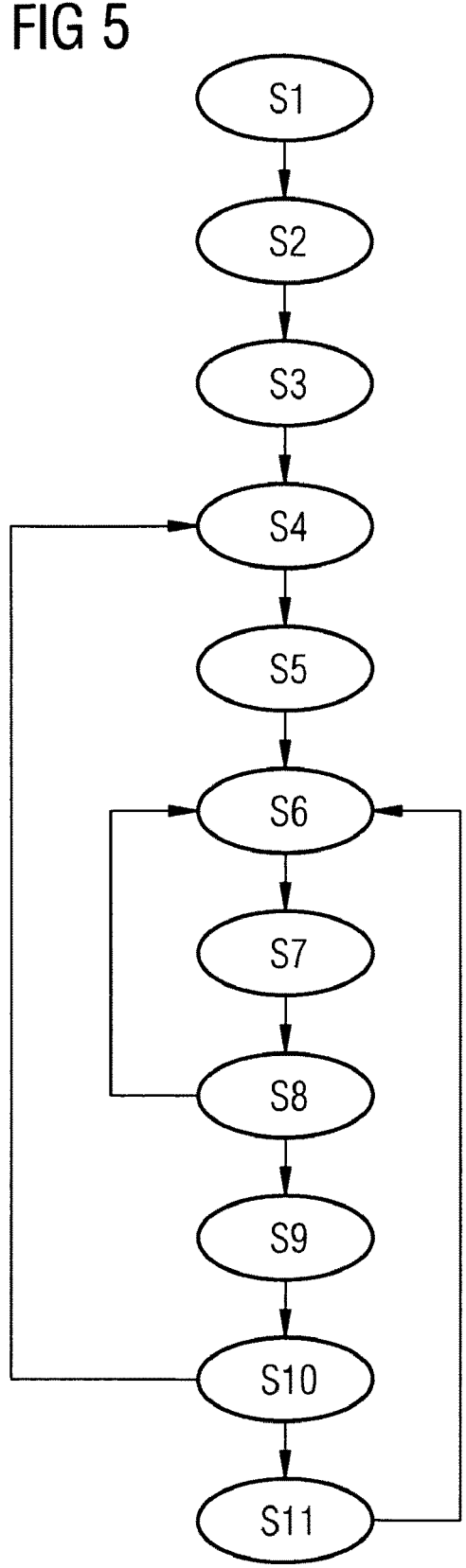
FIG. 5: an overview-type diagram of a flow diagram in accordance with an example embodiment of the invention.

A schematic flow diagram in accordance with a preferred embodiment of the present invention will be explained in greater detail below with reference to FIG. 5.

In a first step S1 image datasets BD from different modalities $M_1$, $M_2$, $M_3$, $M_4$, $M_5$, will be provided. These will be forwarded via the input interface IS to the device 10.

In a second step S2 an image for an image dataset BD will be selected by the user.

In a third step S3 contour lines KL will be created automatically in the respective image datasets BD and integrated into the image dataset BD. To this end the contour line KL will be overlaid with the raw image dataset and stored as a combined image. Optionally it is possible to store the combined image dataset with the contour lines KL separately.

In a fourth step S4 a patient-independent, abstract representation R will be provided. The representation R will preferably be provided from the archive A for the respective image data BD. Typically this can be done using an assignment between the organ to be examined and the respective representation R. In other words stored in the archive A under the keyword "stomach" is at least one representation of the stomach. Likewise a number of representations can also be stored for the other organs (e.g. for the heart) which can relate to different variants of the heart (healthy heart, diseased heart, child's heart, heart with congenital illnesses etc.).

In a fifth step S5 the image datasets are fitted via their contour lines KL into the representation R. this is preferably done by means of the corresponding user interactions. In this case the user selects the respective image dataset BD and identifies in the representation R the point at which the image dataset is to be inserted.

In a sixth step S6, this fitting process will be used as a starting point for calculation and generation of a model M. The model M can be three-dimensional or four-dimensional and relate to image datasets BD that originate from different modalities.

In a seventh step S7 the generated patient-specific model M will be displayed at a user interface UI.

In an eighth step S8 the user can further adapt the generated model M. For example he can still make corrections or refine the model here. In addition he can edit a model M in accordance with other points of view. He can thus create or generate a shunt vitium, he can change or create the course of vessels; he can change the arrangement of the chambers, he can create, change or adapt size relationships or he can create, change or adapt additional structures, such as a bypass operation, the introduction of stents or coils, a vessel graft or new anatomical structures for a planned intervention or for an operation or example. In addition to manual adaptation and automatic adaptation of the generated model M can also be provided. These automatic adaptation measures can for example include pattern recognition measures or other interpolation measures from medical information technology.

In a ninth step S9 the generated model M is stored.

In a further tenth step S10 a new representation R can be created from the generated model M. This is indicated in FIG. 5 with the arrow leading from step S10 to step S4. The new representation R can likewise be stored in the archive A for future access.

In an eleventh step S11 further image datasets BD can be inserted into the generated model M. This is intended to be identified in FIG. 5 by the arrow leading from step S11 to step S6. This allows the generated model M to be dynamically refined.

Created in the archive A is so to speak a three-dimensional or four-dimensional library for representations R. The basis for this representation library is formed by a set of unprocessed representations for the most frequently occurring cardiac diseases, such as for a ventricular septum defect, for an atrial septum defect, for a Fallot's tetralogy, for a transposition of the large arteries or for uncorrected shunt vities.

A significant advantage of an embodiment of the present invention can be seen in the fact that, in addition to a monomodal approach a multimodal approach can also be adopted. With the monomodal approach only image datasets BD from a specific modality are used. In the multimodal approach different image datasets are combined and integrated into a model, meaning that a number of modalities are taken into consideration (e.g. ultrasound data, heart catheter data, CT data, etc.).

A further advantage of an embodiment is to be seen in the fact that the created model M can be supplemented by additional information Z. The additional information Z can include morphological and non-morphological information. Above and beyond this further functional information can also be inserted which has been detected for example from the measured flow speeds in the ultrasound Doppler method.

A further advantage of an embodiment is to be seen in the high flexibility, in that the model M can be represented according to any given viewpoints. For example separate three-dimensional structures can be marked and selected. In addition specific structures can be displayed that are relevant for example for a planned intervention or an operation. For example, precisely the structures can be selected and made visible in the model M that are relevant for the implantation of a heart pacemaker stimulation probe in the coronary vein sinus.

In the automatic creation and insertion of the contour lines KL into the image datasets BD there can be reference back to known methods, in which for example polygons are generated in relation to the endocard or pericard. In an advantageous embodiment the user can accept the suggestion for the automatically-generated contour lines KL or he can still adapt these manually by moving the contour line or adapting it in some other way. Likewise the user has the opportunity at any given time to adapt the further automatic suggestions in accordance with the method or to refine them.

Basically there is provision in accordance with an embodiment of the invention for two application scenarios:
In a first application context, two-dimensional image datasets and/or three-dimensional image datasets are provided for which a three-dimensional or four-dimensional model will then be created;
in a second application context there is provision for a three-dimensional or four dimensional model to already exist that will be refined by further image datasets (in a variable dimension); this refinement can be executed successively by accepting the further image datasets into the model M.

In an advantageous development, there is provision for an embodiment of the method to include an additional method step, namely a semi-automatic calibration and adaptation of the size relationships. This enables the model M to be refined and improved even more.

Advantageously relevant image information can be linked in the generated model M to further patho-physiological fundamentals of the respective disease. For example the pediatric cardiologist is able, with the generated model M, to determine the symptoms of the disease at a glance and in a visually very easily recognizable manner. The generated model M can be included as the basis for further clinical processes or interventions (e.g. as an operation planning model). Likewise the model M can be further developed with simple graphical tools after the end of the therapy so that the model can be visually adapted to reflect the course of the disease over time.

For a better and easier identification of relevant structures there can be provision for the model M to be subject to even further image processing, such as for example color adaptations, a selection of relevant structures, highlighted identification of relevant structures and image processing processes for increasing the image quality.

Preferably the representation R involves a schematic (two- or three-dimensional) representation of the respective organ (e.g. of the heart). The organ is represented structurally in the representation R and independent of the respective patient. A representation R does not thus contain any patient-specific data but nearly image data which can for example be used as a framework for a representation of the heart.

In accordance with an advantageous development, an embodiment of the method includes a number of interpolation steps. If for example a first slice is introduced into the model and in a second step a second slice, interpolation also enables all slices between the first and the second slice to be automatically calculated and introduced into the model M. This has the advantage for the user that he has to carry out fewer manual steps and only has to insert a few slices manually into the three-dimensional model M. Advantageously he can correct the automatically-generated and interpolated model M manually at any time. However the quality of the generated model M basically increases with the number of slices fitted into it.

To conclude, it should be pointed out that the description of the invention and the example embodiments are basically not to be understood as being restrictive in respect of a specific physical realization of the invention. For a suitable person skilled in the art it is especially evident that the invention can be realized partly or completely in software and/or in hardware and/or distributed over a number of physical products— especially including computer program products.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combineable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

LIST OF REFERENCE SYMBOLS

10 Device
BD Image dataset
$M_1$ Ultrasound device
$M_2$ Heart catheter
$M_3$ Nuclear magnetic resonance device
$M_4$ CT or MRT
$M_5$ EKG device
IS Input interface
R Representation
A Archive
KL Contour line
K Contour module
I Integrator
Z Information covering a number of image datasets

What is claimed is:

1. Computer-implemented method for creating a model from a number of medical image datasets, comprising:
providing a number of medical image datasets, the medical image datasets being acquired or having been acquired from same or from different modalities;
automatically creating contour lines in the medical image datasets provided;
providing a representation;

semi-automatically fitting the created contour lines into the representation provided, and merging the provided medical image datasets to create the model for the medical image datasets; and displaying the created model for the medical image datasets.

2. The method as claimed in claim 1, wherein the medical image datasets are two-dimensional, three-dimensional or four-dimensional.

3. The method as claimed in claim 2, wherein further two- or three-dimensional medical image datasets are able to be fitted into the representation, the representation being three-dimensional representation.

4. The method as claimed in claim 2, wherein the model is three- or four-dimensional.

5. The method as claimed in claim 1, wherein further two- or three-dimensional medical image datasets are able to be fitted into the representation, the representation being three-dimensional representation.

6. The method as claimed in claim 5, wherein the calculation of the model includes an interpolation of previously fitted slices or two-dimensional image datasets to further image datasets or to further slices in the three-dimensional representation.

7. The method as claimed in claim 1, wherein the creation of the contour lines is able to include a manual adaptation of the contour lines.

8. The method as claimed in claim 1, wherein the providing of the medical image datasets includes an automatic adaptation of the presentation parameters.

9. The method as claimed in claim 1, wherein the model is three- or four-dimensional.

10. The method as claimed in claim 9, wherein the model includes information encompassing a number of medical image datasets.

11. The method as claimed in claim 1, wherein the model includes information encompassing a number of medical image datasets.

12. The method as claimed in claim 1, wherein the model includes at least one of absolute and relative specifications.

13. The method as claimed in claim 12, wherein the relative specifications are size specifications.

14. The method as claimed in claim 1, wherein the calculation of the model includes a manual adaptation of the model.

15. The method as claimed in claim 1, wherein the model is at least one of editable and navigable.

16. The method as claimed in claim 1, wherein the calculated model is storable in an archive and used unchanged or changed as a basis for a further representation.

17. The method of claim 1, wherein the method is executed by a computer performing a computer program including commands readable by the computer for executing the method when the commands are executed on the computer.

18. A tangible computer readable medium including program segments for, when executed on a computer device, causing the computer device to implement the method of claim 1.

19. A computer-implemented device for creating a model from a number of medical image datasets, comprising:
at least one input interface to a number of different modalities, with each respective one of the modalities being designed to provide at least one medical image dataset, the number of medical image datasets being acquired or having been acquired from different modalities via the input interface;
at least one contour module, designed for automatic creation of contour lines in the medical image datasets provided, received via the input interface;
an archive, designed for providing at least one representation;
an integrator, designed for semi-automatic fitting of the medical image datasets into the representation provided and for merging the medical image datasets to create the model for the medical image datasets; and
a graphical user interface, designed for displaying the calculated model for the medical image datasets.

20. The computer-implemented device as claimed in claim 19, wherein the medical image datasets are two-dimensional, three-dimensional or four-dimensional.

* * * * *